United States Patent [19]

Carlsson et al.

[11] Patent Number: 4,746,667
[45] Date of Patent: May 24, 1988

[54] PHARMACEUTICAL COMPOSITION CONTAINING 2-(2-BENZIMIDAZOLYL THIOMETHYL) PYRIDINE

[75] Inventors: Enar I. Carlsson, Västra Frölunda; Håkan S. Larsson, Rävlanda; Gunhild W. von Wittken Sundell, Askim; Viola I. Samuelsson-Junggren, Mölnlycke; Kenneth Lundström, Svanesund, all of Sweden

[73] Assignee: Aktiebolaget Hassle, Sweden

[21] Appl. No.: 939,274

[22] Filed: Dec. 10, 1986

Related U.S. Application Data

[63] Continuation-in-part of Ser. No. 804,328, Dec. 4, 1985, abandoned, which is a continuation of Ser. No. 620,527, Jun. 12, 1984, abandoned, which is a continuation of Ser. No. 400,388, Jul. 21, 1982, abandoned.

[30] Foreign Application Priority Data

Aug. 13, 1981 [SE] Sweden .................. 8104811

[51] Int. Cl.$^4$ .................................. A61K 31/415
[52] U.S. Cl. ............................. 514/338; 546/271
[58] Field of Search ............................. 514/338

[56] References Cited

U.S. PATENT DOCUMENTS

| | | | |
|---|---|---|---|
| 4,045,563 | 8/1977 | Berntsson et al. | 546/271 |
| 4,045,664 | 8/1977 | Berntsson et al. | 546/271 |
| 4,182,766 | 1/1980 | Krasso et al. | 424/270 |
| 4,255,431 | 3/1981 | Junggren et al. | 514/338 |
| 4,337,257 | 6/1982 | Junggren et al. | 424/263 |
| 4,359,465 | 11/1982 | Ruwart | 514/338 |

FOREIGN PATENT DOCUMENTS

| | | |
|---|---|---|
| 890024 | 8/1980 | Belgium . |
| 0005129 | 4/1981 | European Pat. Off. . |
| 0045200 | 7/1981 | European Pat. Off. . |
| 1500043 | 2/1975 | United Kingdom . |
| 1525958 | 10/1975 | United Kingdom . |

OTHER PUBLICATIONS

Berntsson et al. Chem. Abst. 96:68986p, 91:193309t, 91:157736w.

Aktiebolag Hassle, Chem. Abst. 88:105333f.
Varga et al., Chem. Abst. vol. 83, 201872y.

*Primary Examiner*—Jane T. Fan
*Attorney, Agent, or Firm*—Brumbaugh, Graves, Donohue & Raymond

[57] ABSTRACT

A pharmaceutical preparation containing as active ingredient a compound of the formula

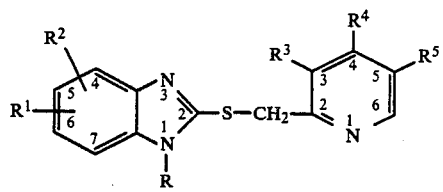

or a therapeutically acceptable salt thereof in which formula $R^1$ and $R^2$ are the same or different and each selected from the group consisting of H, $CF_3$, $NO_2$, $-COOCH_3$, $-COOC_2H_5$, alkyl containing 1-7 carbon atoms, halogen, alkoxy, containing 1-5 carbon atoms, and alkanoyl containing 1-4 carbon atoms;

R is selected from the group consisting of H, alkanoyl containing 1-4 carbon atoms, and carboalkoxy containing 2-6 carbon atoms; and $R^3$, $R^4$ and $R^5$, which are the same or different, are each selected from the group consisting of H, $CH_3$, $C_2H_5$, $OCH_3$, $OC_2H_5$, $OCH_2CH_2OCH_3$, and $OCH_2CH_2OCH_2CH_3$; provided that (a) at least one of $R^3$, $R^4$ and $R^5$ is selected from the group consisting of $CH_3$, $C_2H_5$, $OCH_3$, $OC_2H_5$, $OCH_2CH_2OCH_3$, and $OCH_2CH_2OCH_2CH_3$, and (b) when two of $R^3$, $R^4$ and $R^5$ are H, then the remaining radical $R^3$, $R^4$ or $R^5$ is selected from the group consisting of $OCH_3$, $OC_2H_5$, $OCH_2CH_2OCH_3$, and $OCH_2CH_2OCH_2CH_3$;

the use of the compounds for inhibiting gastric acid secretion; compounds included in the formula I, and processes for their preparation.

3 Claims, No Drawings

PHARMACEUTICAL COMPOSITION CONTAINING 2-(2-BENZIMIDAZOLYL THIOMETHYL) PYRIDINE

This application is a continuation-in-part of application Ser. No. 804,328, filed on Dec. 4, 1985 now abandoned which is a continuation of application Ser. No. 620,527, filed on 6/12/84, now abandoned, which is a continuation of application Ser. No. 400,388, filed on July 21, 1982 now abandoned.

DESCRIPTION

1. Field of the Invention

The object of the present invention is to provide compounds which inhibit exogenously or endogenously stimulated gastric acid secretion and thus can be used in the treatment of peptic ulcer.

The present invention relates to the use of a group of benzimidazole derivatives, or therapeutically acceptable salts thereof, for inhibiting gastric acid secretion in mammals and man. In a more general sense, the invention relates to the use of the compounds for treatment of gastrointestinal inflammatory diseases in mammals and man, including i.e. gastric and duodenal ulcer. Furthermore it relates to the use of these compounds for treatment of other gastrointestinal disorders, where a gastric antisecretory effect is desirable i.e. in patients with gastrinomas and in patients with acute upper gastrointestinal bleeding. The invention also relates to pharmaceutical compositions containing at least one member of the said group of benzimidazole derivatives, or a therapeutically acceptable salt thereof, as active ingredient. In a further aspect, the invention relates to new compounds, and therapeutically acceptable salts thereof, within the said group of benzimidazole derivatives, and to processes for preparation of such new compounds.

2. Prior Art

Benzimidazole derivatives intended for inhibiting gastric acid secretion are disclosed in the British patent specification Nos. 1 500 043 and 1 525 958, in the U.S. Pat. No. 4,182,766 and in the European patent specification No. 0 005 129.

THE INVENTION

It has been found that the compounds of the formula

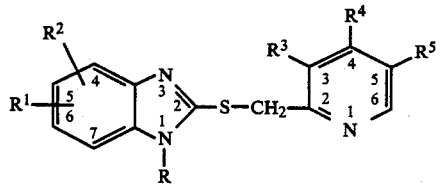

and therapeutically acceptable salts thereof in which formula $R^1$ and $R^2$ are the same or different and each selected from the group consisting of H, $CF_3$, $NO_2$, $-COOCH_3$, $-COOC_2H_5$, alkyl containing 1-7 carbon atoms, halogen, alkoxy containing 1-5 carbon atoms, and alkanoyl containing 1-4 carbon atoms;

R is selected from the group consisting of H, alkanoyl containing 1-4 carbon atoms, and carboalkoxy containing 2-6 carbon atoms; and $R^3$, $R^4$ and $R^5$, which are the same or different, are each selected from the group consisting of H, $CH_3$, $C_2H_5$, $OCH_3$, $OC_2H_5$, $OCH_2CH_2OCH_3$, and $OCH_2CH_2OCH_2CH_3$, provided that (a) at least one of $R^3$, $R^4$ and $R^5$ is selected from the group consisting of $CH_3$, $C_2H_5$, $OCH_3$, $OC_2H_5$, $OCH_2CH_2OCH_3$, and $OCH_2CH_2OCH_2CH_3$, and (b) when two of $R^3$, $R^4$ and $R^5$ are H, then the remaining radical $R^3$, $R^4$ or $R^5$ is selected from the group consisting of $OCH_3$, $OC_2H_5$, $OCH_2CH_2OCH_3$, and $OCH_2CH_2OCH_2CH_3$;

are effective as inhibitors of gastric acid secretion in mammals and man. The compounds of the formula I, and therapeutically acceptable salts thereof, are stable in gastric juice, which is of importance at oral administration.

Illustrative examples of the radicals in the formula I are:

Alkyl groups $R^1$ and $R^2$: methyl, ethyl, n-propyl, i-propyl, n-butyl, sec.-butyl, isobutyl, tert.-butyl, n-pentyl, n-hexyl, n-heptyl. It is preferred that alkyl groups $R^1$ and $R^2$ contains 1, 2, 3 or 4 carbon atoms. The preferred alkyl group is methyl.

Halogen $R^1$ and $R^2$: chloro, bromo, fluoro, iodo. The preferred halogen groups are chloro and bromo.

Alkoxy groups $R^1$ and $R^2$: methoxy, ethoxy, n-propoxy, i-propoxy, n-butoxy, sec.-butoxy, isobutoxy, tert.-butoxy, n-pentoxy. It is preferred that alkoxy groups $R^1$ and $R^2$ contain 1, 2 or 3 carbon atoms. The preferred alkoxy group is methoxy.

Alkanoyl groups R, $R^1$ and $R^2$: HCO—, $CH_3CO$—, $CH_3CH_2CO$—, $CH_3CH_2CH_2CO$—,

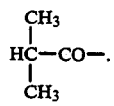

The preferred alkanoyl group $R^1$ and $R^2$ is $CH_3CO$. The preferred alkanoyl group R is $CH_3CO$.

Carboalkoxy groups R:

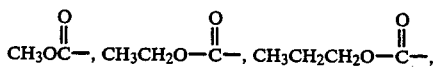

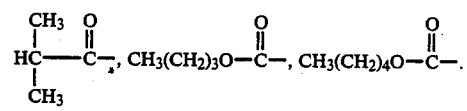

It is preferred that carboalkoxy groups R contains 2 or 3 carbon atoms. Thus, the groups $CH_3OCO$— and $CH_3CH_2OCO$— are preferred.

The preferred meaning of the radical R is H.

Preferred combinations of the radicals in the formula I, subject to the two provisos (a) and (b) given above, are given in Table 1 below.

TABLE 1

| Preferred combinations of $R^1$, $R^2$, R, $R^3$, $R^4$ and $R^5$ | | |
|---|---|---|
| $R^1$ and $R^2$, the same or different if not indicated otherwise | R | $R^3$, $R^4$ and $R^5$, the same or different if not indicated otherwise |
| H, $COOCH_3$, $COOC_2H_5$ alkyl, halogen, alkoxy, alkanoyl | H | H, $CH_3$, $C_2H_5$, $OCH_3$ $OC_2H_5$, $OCH_2CH_2OCH_3$, $OCH_2CH_2OCH_2CH_3$ |
| H, $COOCH_3$, $CH_3$, Cl, Br, $OCH_3$, $CH_3CO$ | H | H, $CH_3$, $C_2H_5$, $OCH_3$, $OCH_2CH_2OCH_3$ |
| H, $COOCH_3$, $CH_3$, $OCH_3$, $CH_3CO$ | H | $CH_3$, $OCH_3$ |

TABLE 1-continued

| R¹ and R², the same or different if not indicated otherwise | R | R³, R⁴ and R⁵, the same or different if not indicated otherwise |
|---|---|---|
| H, COOCH₃, alkyl alkoxy, alkanoyl | H | H, CH₃, OCH₃, OC₂H₅ |
| H, COOCH₃, COOC₂H₅, alkyl, halogen, alkoxy, alkanoyl | H | R³: CH₃<br>R⁴: OCH₃<br>R⁵: CH₃ |
| H, COOCH₃, COOC₂H₅ alkyl, alkoxy, alkanoyl | H | R³: H<br>R⁴: OCH₃<br>R⁵: CH₃ |
| NO₂, CF₃ | H | R³: CH₃<br>R⁴: OCH₃<br>R⁵: CH₃ |
| H, COOCH₃, COOC₂H₅, alkyl, alkoxy, alkanoyl | H | R³: CH₃<br>R⁴: OCH₃<br>R⁵: H |
| H, COOCH₃, COOC₂H₅, alkyl, alkoxy, alkanoyl | H | R³: H<br>R⁴: OCH₃<br>R⁵: H |
| H, COOCH₃, COOC₂H₅, alkyl, alkoxy, alkanoyl | H | R³: CH₃<br>R⁴: H<br>R⁵: CH₃ |
| H, COOCH₃, COOC₂H₅, alkyl, alkoxy, alkanoyl | H | R³: H<br>R⁴: OCH₃, OC₂H₅, OCH₂CH₂OCH₃, OCH₂CH₂OCH₂CH₃<br>R⁵: H |
| H, COOCH₃, COOC₂H₅, alkyl, alkoxy alkanyol | H | R³: CH₃<br>R⁴: CH₃<br>R⁵: CH₃ |

The radicals $R^1$ and $R^2$ can be bound to the benzimidazole nucleus in any of the positions 4, 5, 6 and 7 as depicted in formula I. It is preferred that $R^1$ and $R^2$ are in position 5 and/or 6.

Preferred individual compounds among those included in the formula I are given in the following Table 2:

TABLE 2

Preferred individual compounds

| R¹ | R² | R | R³ | 4⁴ | R⁵ |
|---|---|---|---|---|---|
| 5-OCH₃ | H | H | CH₃ | OCH₃ | CH₃ |
| 5-COOCH₃ | H | H | CH₃ | OCH₃ | CH₃ |
| 5-COOCH₃ | 6-CH₃ | H | CH₃ | OCH₃ | CH₃ |
| 5-COCH₃ | 6-CH₃ | H | CH₃ | OCH₃ | CH₃ |
| 5-COCH₃ | H | H | CH₃ | OCH₃ | CH₃ |
| 5-CH₃ | H | H | CH₃ | OCH₃ | CH₃ |
| 5-COCH₃ | 6-CH₃ | H | H | CH₃ | CH₃ |
| 5-OCH₃ | H | H | CH₃ | CH₃ | CH₃ |
| 5-COCH₃ | 6-CH₃ | H | H | OCH₃ | H |
| 5-COOCH₃ | 6-CH₃ | H | CH₃ | OCH₃ | H |
| 5-COCH₃ | 6-CH₃ | H | CH₃ | CH₃ | CH₃ |
| 5-COOCH₃ | 6-CH₃ | H | H | OCH₃ | H |

Further preferred individual compounds are those exemplified in the examples given elsewhere in this specification.

In the prior art cited above, no medicinal use is disclosed for the compounds of the formula I. Thus, the present invention comprises pharmaceutical compositions containing a comppound of the formula I or a therapeutically acceptable salt thereof as active ingredient, and the use of the compounds of the formula I or a therapeutically acceptable salt thereof for inhibiting gastric acid secretion in mammals and man.

The compounds of the formula I wherein $R^1$ and $R^2$ are as defined above except $CF_3$ and $NO_2$, R is H and $R^3$, $R^4$ and $R^5$ are H, $CH_3$, $OCH_3$, $OC_2H_5$, $OCH_2CH_2OCH_3$ or $OCH_2CH_2OCH_2CH_3$ are generically disclosed as chemical intermediates in the European patent No. 0 005 129. The specific compounds disclosed in the following Table 3 are disclosed in the said European Pat. No. 0 005 129.

TABLE 3

Compounds disclosed in European patent no. 0 005 129.

| R | R¹ | R² | R³ | R⁴ | R⁵ | Remark |
|---|---|---|---|---|---|---|
| H | 5-COCH₃ | 6-CH₃ | H | CH₃ | CH₃ | base |
| H | 4-CH₃ | 6-CH₃ | CH₃ | H | CH₃ | hydrochloride |
| H | 5-COCH₃ | 6-CH₃ | CH₃ | CH₃ | CH₃ | base |

The present invention, in so far as it concerns compounds of the formula I by themselves, their pharmaceutically acceptable salts, and processes for their preparations, relates to (i) the compounds of the formula I wherein $R^3$, $R^4$ or $R^5$ is $C_2H_5$ (ii) the compounds of the formula I wherein R is alkanoyl or carboalkoxy (iii) the compounds of the formula I wherein R is H except the compounds wherein R, $R^1$, $R^2$, $R^3$, $R^4$ and $R^5$ are combined as follows:

| R¹ | R² | R | R³ | R⁴ | R⁵ |
|---|---|---|---|---|---|
| 5-COCH₃ | 6-CH₃ | H | H | CH₃ | CH₃ |
| 4-CH₃ | 6-CH₃ | H | CH₃ | H | CH₃ |
| 5-COCH₃ | 6-CH₃ | H | CH₃ | CH₃ | CH₃ |

(iv) the compounds of the formula I wherein $R^1$ and/or $R^2$ are $CF_3$ or $NO_2$.

The preferred compounds within the groups (i), (ii), (iii) and (iv) will comprise the same compounds that are indicated as preferred in Table 1 and Table 2 above, subject to the proviso that the specific compounds listed in Table 3 are excluded.

The compounds of the formula I can be prepared by known methods such as

A. reacting a compound of the formula

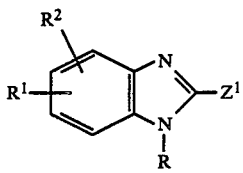

II with a compound of the formula

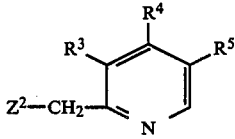

III in which formulas R, $R^1$, $R^2$, $R^3$, $R^4$ and $R^5$ are as defined previosly and wherein one of $Z^1$ and $Z^2$ is SH and the other is a leaving group.

Examples of leaving groups $Z^1$ and $Z^2$ in the compounds II and III are halogens, preferably chlorine, bromine or iodine, acyl radicals, for example, residues of strong organic sulfonic acids, for instance, of an arylsulfonic acid, for example, tosyloxy, or an alkylsulfonic acid, for example, mesyloxy; alkylmercapto groups, for example, methylmercapto; alkylsulfinyl groups, for example, methylsulfinyl and the like.

Thus, $Z^1$ or $Z^2$ when designating leaving groups may be a reactive esterified hydroxy group.

The reaction of a compound of formula II above with a compound of formula III is conveniently carried out in the presence of a suitable solvent that is inert under the reaction conditions utilized as described hereinafter. The reaction may further be carried out in the presence of a suitable base. Suitable bases include, for example, inorganic bases such as sodium or potassium hydroxide, sodium or potassium hydride and the like, organic bases such as tertiary amines, for example, triethylamine and the like.

Suitable solvents for the above described reaction include, for example, alcohols, preferably lower alkanols such as, methanol and ethanol; mixtures of such alcohols with water, ethers, such as, tetrahydrofuran; halogenated hydrocarbons, such as, methylene chloride and chloroform, and the like.

The reaction of the compounds of formulas II and III may be carried out at a temperature between the ambient temperature and the boiling temperature of the reaction mixture. It is preferred to carry out the reaction, however, at a temperature at or close to the boiling point of the reaction mixture for the preparation of a compound of the formula I wherein R is H;

B. reacting a compound of the formula

IV wherein $R^1$ and $R^2$ have the same meaning as given above with a compound of the formula

V wherein $R^3$, $R^4$ and $R^5$ have the same meaning as given above, to the formation of a compound of the formula I wherein R is H;

C. reacting a compound of the formula

VI wherein R, $R^1$ and $R^2$ have the meaning given above and M is K, Na or Li, with a compound of formula

VII wherein $R^3$, $R^4$ and $R^5$ have the meaning given above and $Z^3$ is a reactive esterified hydroxy group, to the formation of a compound of the formula I.

The reactive esterified hydroxy group $Z^3$ may, as in the case of $Z^1$ and $Z^2$, be a hydroxy group esterified with a strong, inorganic or organic acid, preferably a hydrohalogen acid, such as hydrochloric acid, hydrobromic acid, or hydroiodic acid, or esterified with sulfuric acid or with a strong organic sulfonic acid such as a strong aromatic acid, e.g. benzenesulfonic acid, 4-bromobenzenesulfonic acid or 4-toluenesulfonic acid.

D. reduction of a compound of the formula

VIII to the formation of a compound of the formula I:

E. for the preparation of a compound of the formula I wherein the radicals $R^1$ and/or $R^2$ is $COOCH_3$ or $COOC_2H_5$, reacting a compound of the formula

IX wherein R, $R^3$, $R^4$ or $R^5$ are as defined above and wherein $Y^1$ is —COOH, or a functionally equivalent derivative thereof, and $Y^2$ is —COOH, or a functionally equivalent derivative thereof, or $R^1$, with $CH_3OH$      X or $CH_3CH_2OH$      XI or a functionally equivalent derivative thereof, to the formation of a compound of the formula I wherein $R^1$ and/or $R^2$ is $CH_3COO$ or $CH_3CH_2COO$.

This reaction is an ordinary esterification which is carried out in customary manner.

Functionally equivalent derivatives of the hydroxy group in the compounds X and XI are for example halogen such as Cl or Br, or —$N_2$.

Functionally equivalent derivatives of the carboxyl group $Y^1$ and $Y^2$ are for example a metal carboxylate group or an activated carboxyl group, in which case the radicals $Y^1$ or $Y^2$ are for example an acid chloride, an alkyl ester, an acid anhydride or a mixed anhydride with formic esters or carboxylic acids, sulphonic or inorganic esters or derivatives obtained by a reaction between a carboxylic acid and a carbodiimide or similarly functioning compounds such as $N_1N^1$-carbonyl-diimidazole or N-ethyl-5-phenylisoxazolium-$3^1$-sulphonate, the derivative of the carboxyl group $Y^1$ or $Y^2$ being a metal carboxylate group when the hydroxyl group in the compounds X or XI is replaced with halogen. A further functionally equivalent derivative of the carboxyl groups $Y^1$ and $Y^2$ is the group —CN, in which case a cyanide is reacted with a compound of the formula X or XI with subsequent hydrolysis to give a compound of the formula I wherein $R^1$ and/or $R^2$ is $CH_3COO$ or $CH_3CH_2COO$.

F. for the preparation of a compound of the formula I wherein at least one of $R^3$, $R^4$ and $R^5$ is $OCH_3$, $OC_2H_5$, $OCH_2CH_2OCH_3$ or $OCH_2CH_2OCH_2CH_3$, reacting a compound of the formula

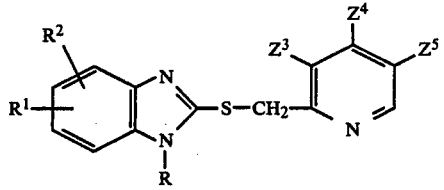
XII wherein R, $R^1$ and $R^2$, are as defined above and $Z^3$, $Z^4$ and $Z^5$ represent either $R^3$, $R^4$ and $R^5$, respektively, or halogen such as Cl, Br, F or I, or $NO_2$, whereby at least one of $Z^3$, $Z^4$ and $Z^5$ represents halogen or $NO_2$, with a compound of the formula $R^6$—O—M  XIII wherein $R^6$ is $CH_3$, $C_2H_5$, $CH_2CH_2OCH_3$ or $CH_2CH_2OCH_2CH_3$, and M is Na, K, or Li, to the formation of a compound of the formula I wherein at least one of $R^3$, $R^4$ and $R^5$ is $OCH_3$, $OC_2H_5$, $OCH_2CH_2OCH_3$ or $OCH_2CH_2OCH_2CH_3$;

G. for the preparation of a compound of the formula I wherein at least one of $R^3$, $R^4$ and $R^5$ is $OCH_2CH_2OCH_3$ or $OCH_2CH_2OCH_2CH_3$, reacting a compound of the formula

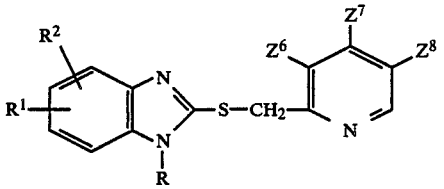
XIV wherein R, $R^1$ and $R^2$ are as defined above, and $Z^6$, $Z^7$ and $Z^8$ represent either $R^3$, $R^4$ and $R^5$, respektively, or a radical $OCH_2CH_2Y$  XV where Y is halogen, whereby at least one of $Z^6$, $Z^7$ and $Z^8$ represent $OCH_2CH_2Y$, with a compound of the formula $R^7$—O—M  XVI wherein $R^7$ is $CH_3$ or $CH_2CH_3$ and M is Na, K or Li, to the formation of a compound of the formula I wherein at least one of $R^3$, $R^4$ and $R^5$ is $OCH_2CH_2OCH_3$ or $OCH_2CH_2OCH_2CH_3$.

Method F and Method G represent the known Williamson ether synthesis and is carried out in known manner.

H. for the preparation of a compound of the formula I wherein R is H, hydrolyzing a compound of the formula

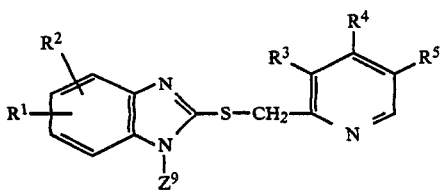
XVII wherein $R^1$, $R^2$, $R^3$, $R^4$ and $R^5$ are as defined above and $Z^9$ is an alkanoyl group or a carboalkoxy group, to the formation of a compound of the formula I wherein R is H.

The radical $Z^9$ can be an alkanoyl group containing 1-6 carbon atoms or a carboalkoxy group containing 2-6 carbon atoms.

I. reduction of a compound of the formula

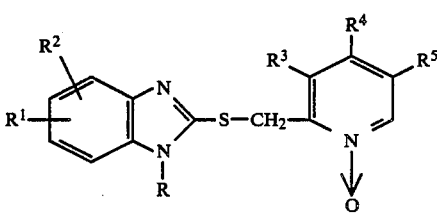
XVIII to the formation of a compound of the formula I.

J. reduktion of a compound of the formula

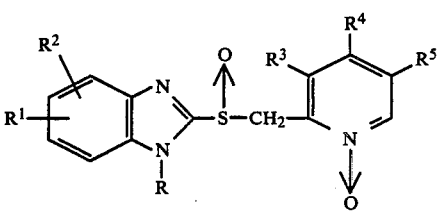
XIX to the formation of a compound of the formula I.

Depending on the process conditions and the starting materials, the end product of the formula I is obtained either as the free base or as a salt. Both the free base and the salts of the end products are included within the scope of the invention. Thus, basic, neutral or mixed salts may be obtained as well as hemi, mono, sesqui or polyhydrates. Acid addition salts of the new compounds may in a manner known per se be transformed into free base using basic agents such as alkali or by ion exchange. The free bases obtained may also form salts with organic or inorganic acids. In the preparation of acid addition salts preferably such acids are used which form suitable therapeutically acceptable salts. Examples of such acids are hydrohalogen acids, sulfonic acid, phosphoric acid, nitric acid, and perchloric acid; aliphatic, alicyclic, aromatic or heterocyclic carboxyl or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, phenylacetic acid, benzoic acid, p-aminobenzoic acid, p-hydroxybenzoic acid, salicylic acid or p-aminosalicylic acid, embonic acid, methanesulfonic acid, ethanesulfonic acid, hydroxyethanesulfonic acid, ethylenesulfonic acid, halogenbenzenesulfonic acid, toluenesulfonic acid, naphtylsulfonic acid or sulfanilic acids; methionine, tryptophane, lysine or arginine.

These or other salts of the new compounds, as e.g. picrates, may serve as purifying agents of the free bases obtained. Salts of the bases may be formed, separated from solution, and then the free base can be recovered in higher purity from a new salt solution.

The starting materials utilized in the processes A–J are known or may, if they should be new, be obtained according to processes known per se.

In clinical use the active compounds of the formula I will normally be administered orally, rectally or by injection in the form of a pharmaceutical preparation which contains the active component either in the form of the free base or in the form of a pharmaceutically acceptable, non-toxic salt, as described earlier, optionally in combination with a pharmaceutically acceptable carrier. The carrier may be in the form of a solid, semisolid or liquid diluent, or a capsule. These pharmaceutical preparations are a further object of the invention. The compounds may also be used without carrier material. Usually the amount of active compound is between 0.1 and 99% by weight of the preparation, for example between 0.5 to 20% by weight in preparations for injection and between 2 and 50% by weight in preparations for oral administration.

In the preparation of pharmaceutical preparations containing a compound of the formula I in the form of dosage units for oral administration, the active compound may be mixed with a solid, pulverulent carrier, such as lactose, saccharose, sobitol, mannitol, a starch such as potatoe starch, corn starch, or amylopectin, cellulose derivatives or gelatin, and may also include a lubricant such as magnesium stearate, calcium stearate or polyethyleneglycol waxes. The mixture is then pressed into tablets. If coated tablets are desired, a core prepared as described above may be coated with a concentrated sugar solution which may contain gum arabic, gelatin, talc, tatanium dioxide or alternatively with a lacquer dissolved in volatile organic solvents or mixtures of solvents. To this coating various dyes may be added in order to distinguish tablets with different active compounds or with different amounts of the active compound present.

Soft gelatin capsules may be prepared which capsules contain a mixture of the active compound or compounds and vegetable oil. Hard gelatin capsules may contain granules of the active compound in combination with a solid, pulverulent carrier as lactose, saccharose, sorbitol, mannitol, potato starch, corn starch, amylopectin, cellulose derivatives or gelatin.

Dosage units for rectal administration may be prepared in the form of suppositories which contain the active substance in admixture with a neutral fatty base, or they may be prepared in the form of gelatin-rectal capsules which contain the active substance in admixture with a vegetable oil or with paraffin oil.

Liquid preparations for oral administration may be prepared in the form of syrups or suspensions, e.g. solutions containing from 0.2% to 20% by weight of the active ingredient, the remainder comprising for example sugar and a mixture of ethanol, water, glycerol and propylene glycol. If desired, such liquid preparations may contain colouring agents, flavouring agents, saccharin and carboxymethylcellulose as a thickening agent.

Solutions for parenteral administration by injection may be prepared as sterile solution, for example in pyrogen-free water, of a water soluble pharmaceutically acceptable salt of the active compound, preferably in a concentration from 0.5% to 10% by weight. These solutions may also contain stabilizing agents and/or buffering agents and may be manufactured in different dosage unit ampoules.

The dosage at which the active substance are administered may vary within a wide range and will depend on various factors such as for example the individual requirements of each patient and the manner of administration. In general, oral dosages will be in the range from 100 to 400 mg/day of active substance and intravenous dosages in a range from 5 to 20 mg/day.

The invention is illustrated by the following examples.

EXAMPLE 1

Method A. Preparation of
2-[2-(3,5-dimethyl-4-methoxy)pyridylmethylthio]-5-$COCH_3$-6-$CH_3$-benzimidazole 22.2 g (0.1 mole) of 3,5-dimethyl-4-methoxy-2-chloromethylpyridine hydrochloride and 20.6 g (0.1 mole) of 5-$COCH_3$-6-$CH_3$-2-mercapto benzimidazole was dissolved in 250 ml methanol whereafter 4 g (0.1 mole) NaOH dissolved in 25 ml $H_2O$ was added. The mixture was heated to reflux and an additional amount of 4 g (0.1 mole) NaOH in 25 ml $H_2O$ was added dropwise during 15 min. The mixture was thereafter refluxed during 6 hours whereafter it was cooled and diluted with 500 ml $H_2O$. The resulting mixture was extracted with $CH_2Cl_2$, dried and evaporated. The remainder was recrystallized from acetonitrile giving the title substance in the form of free base. Yield: 30 g (85% of the theoretical yield). M.P.: 139° C.

EXAMPLES 2-50

The compounds indentified by example numbers 2–50 in the following Table 4 were prepared using the same method of preparation as in Example 1. The compounds were obtained in the form of their free base. The compound of Example 1 is also included in the table.

TABLE 4
Identifying data for compounds of the invention

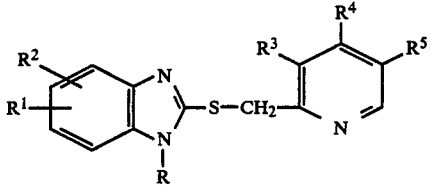

| Example no | R¹ | R² | R | R³ | R⁴ | R⁵ | M.p. °C. |
|---|---|---|---|---|---|---|---|
| 1 | 5-COCH₃ | 6-CH₃ | H | H | CH₃ | CH₃ | 148 |
| 2 | 5-COOCH₃ | 6-CH₃ | H | H | CH₃ | CH₃ | 125 |
| 3 | 5-COOCH₃ | H | H | H | CH₃ | CH₃ | 136 |
| 4 | 5-COCH₃ | 6-CH₃ | H | CH₃ | CH₃ | H | 140 |
| 5 | 5-COOCH₃ | 6-CH₃ | H | CH₃ | CH₃ | H | 170 (oil) |
| 6 | 4-CH₃ | 6-CH₃ | H | CH₃ | H | CH₃ | 206 |
| 7 | 5-COCH₃ | 6-CH₃ | H | CH₃ | H | CH₃ | 125 |
| 8 | 5-COCH₃ | 6-CH₃ | H | CH₃ | CH₃ | CH₃ | 100 (oil) |
| 9 | 5-COCH₃ | 6-CH₃ | H | H | OCH₃ | H | 97 |
| 10 | 4-CH₃ | 6-CH₃ | H | H | OCH₃ | H | 110 |
| 11 | 5-COCH₃ | 6-CH₃ | H | CH₃ | OCH₃ | CH₃ | 139 |
| 12 | 5-COOCH₃ | 6-CH₃ | H | CH₃ | H | CH₃ | 130 |
| 13 | 5-COOCH₃ | 6-CH₃ | H | CH₃ | CH₃ | CH₃ | 184 |
| 14 | 5-COOCH₃ | 6-CH₃ | H | H | OCH₃ | H | 146 |
| 15 | 5-COOCH₃ | 6-CH₃ | H | H | OC₂H₅ | H | 90–94 |
| 16 | 5-COOCH₃ | 6-CH₃ | H | CH₃ | OCH₃ | H | 160 |
| 17 | 5-COOCH₃ | 6-CH₃ | H | CH₃ | OCH₃ | CH₃ | 119 |
| 18 | 5-COOCH₃ | 6-CH₃ | H | H | OCH₃ | CH₃ | 184 |
| 19 | 5-COOCH₃ | H | H | CH₃ | H | CH₃ | 130 |
| 20 | 5-COOCH₃ | H | H | CH₃ | OCH₃ | CH₃ | 175 |
| 21 | 5-COCH₃ | H | H | CH₃ | OCH₃ | CH₃ | 122–124 |
| 22 | 5-OCH₃ | H | H | H | OCH₃ | CH₃ | 168 |
| 23 | 5-OCH₃ | H | H | CH₃ | OCH₃ | CH₃ | 110–119 |
| 24 | 5-CH₃ | H | H | CH₃ | OCH₃ | CH₃ | 148 |
| 25 | H | H | H | CH₃ | OCH₃ | CH₃ | 125 |
| 26 | 5-Cl | H | H | CH₃ | OCH₃ | CH₃ | 180 |
| 27 | 5-CH₃ | H | H | H | OC₂H₄OCH₃ | H | 100 |
| 28 | 5-COOC₂H₅ | H | H | CH₃ | OCH₃ | CH₃ | 130 |
| 29 | 5-OCH₃ | H | H | CH₃ | CH₃ | CH₃ | 157 |
| 30 | CH₃ | CH₃ | H | CH₃ | CH₃ | H | 140 |
| 31 | COOCH₃ | CH₃ | H | CH₃ | H | CH₃ | 125 |
| 32 | 5-C(CH₃)₃ | H | H | CH₃ | OCH₃ | CH₃ | |
| 33 | 5-NO₂ | H | H | CH₃ | OCH₃ | CH₃ | |
| 34 | 5-CH₃ | 6-CH₃ | H | CH₃ | OCH₃ | CH₃ | |
| 35 | 4-CH₃ | 6-CH₃ | H | CH₃ | OCH₃ | CH₃ | |
| 36 | 5-C₂H₅ | H | H | CH₃ | OCH₃ | CH₃ | |
| 37 | 5-CF₃ | H | H | CH₃ | OCH₃ | CH₃ | |
| 38 | 5-CH(CH₃)₂ | H | H | CH₃ | OCH₃ | CH₃ | |
| 39 | 5-Cl | 6-Cl | H | CH₃ | OCH₃ | CH₃ | |
| 40 | 5-OC₂H₅ | H | H | CH₃ | OCH₃ | CH₃ | |
| 41 | 5-Br | H | H | CH₃ | OCH₃ | CH₃ | |
| 42 | 5-OCH₃ | H | H | OCH₃ | H | H | |
| 43 | 5-Cl | H | H | CH₃ | CH₃ | H | |
| 44 | 5-OCH₃ | H | H | CH₃ | CH₃ | H | |
| 45 | 5-CH₃ | 7-CH₃ | H | CH₃ | CH₃ | H | |
| 46 | 5-OCH₃ | H | H | CH₃ | OCH₃ | H | |
| 47 | 5-COOCH₃ | 7-CH₃ | H | CH₃ | CH₃ | H | |
| 48 | 5-COCH₃ | H | H | CH₃ | CH₃ | H | |
| 49 | 5-OCH₃ | H | H | CH₃ | OC₂H₅ | CH₃ | |
| 50 | 5-COOCH₃ | 6-CH₃ | H | H | OCH₃ | C₂H₅ | |

Identifying data for the compounds according to examples 32–50 are given in the following Table 5.

TABLE 5
NMR data for compounds of the invention

| Compound according to example no. | NMR data δ |
|---|---|
| 32 | 1.37 (s,9H), 2.26 (s,3H), 2.30 (s,3H), 3.76 (s,3H), 4.37 (s,2H), 7.25 (k,1H), 7.49 (d,1H), 7.57 (d,1H), 8.30 (s,1H) |
| 33 | 2.21 (s,3H), 2.31 (s,3H), 3.75 (s,3H), 4.77 (s,2H), 7.64 (d,1H), 8.11 (k,1H), 8.23 (s,1H), 8.36 (d,1H) |
| 34 | 2.23 (s,3H), 2.28 (s,3H), 2.33 (s,6H), 3.75 (s,3H), 4.33 (s,2H), 7.29 (s,2H), 8.23 (s,1H) |
| 35 | 2.28 (s,3H), 2.33 (s,3H), 2.43 (s,3H), 2.58 (s,3H), 3.81 (s,3H), 4.42 (s,2H), 6.92 (s,1H), 7.29 (s,1H), 8.36 (s,1H) |
| 36 | 1.25 (t,3H), 2.25 (s,3H), 2.30 (s,3H), 2.72 (k,2H), 3.76 (s,3H), 4.38 (s,2H), 7.02 (k,1H), 7.35 (d,1H), 7.45 (d,1H), 8.26 (s,1H) |
| 37 | 2.31 (s,3H), 2.35 (s,3H), 3.84 (s,3H), 4.46 (s,2H), 7.51 (k,1H), 7.70 (d,1H), 7.92 (d,1H), 8.38 (s,1H) |

TABLE 5-continued

NMR data for compounds of the invention

| Compound according to example no. | NMR data δ |
|---|---|
| 38 | 1.25 (s,3H), 1.33 (s,3H), 2.27 (s,3H), 2.33 (s,3H), 3.03 (m,1H), 3.80 (s,3H), 4.51 (s,2H), 7.17 (k,1H), 7.53 (d,1H), 7.58 (d,1H), 8.36 (s,1H) |
| 39 | 2.22 (s,3H), 2.31 (s,3H), 3.81 (s,3H), 4.72 (s,2H), 7.76 (s,2H), 8.23 (s,1H) |
| 40 | 1.41 (t,3H), 2.30 (s,3H), 2.35 (s,3H), 3.82 (s,3H), 4.10 (k,2H), 4.39 (s,2H), 6.92 (k,1H), 7.14 (d,1H), 7.52 (d,1H), 8.40 (s,1H) |
| 41 | 2.16 (s,3H), 2.26 (s,3H), 3.71 (s,3H), 4.68 (s,2H), 7.23 (k,1H), 7.43 (d,1H), 7.65 (d,1H), 8.18 (s,1H) |
| 42 | 3.80 (s,3H), 3.83 (s,3H), 4.50 (s,2H), 6.90 (k,1H), 7.15 (d,1H), 7.24 (m,2H), 7.53 (d,1H), 8.23 (k,1H) |
| 43 | 2.33 (s,3H), 2.35 (s,3H), 4.80 (s,2H), 7.19 (m,2H), 7.52 (d,1H), 7.58 (d,1H), 8.34 (d,1H) |
| 44 | 2.34 (s,6H), 3.85 (s,3H), 4.51 (s,2H), 6.89 (k,1H), 7.15 (d,1H), 7.15 (d,1H), 7.53 (d,1H), 8.41 (d,1H) |
| 45 | 2.16 (s,6H), 2.38 (s,3H), 2.53 (s,3H), 4.46 (s,2H), 6.86 (s,1H), 6.99 (d,1H), 7.25 (s,1H), 8.20 (d,1H) |
| 46 | 2.26 (s,3H), 3.86 (s,3H), 3.91 (s,3H), 4.70 (s,2H), 6.87 (m,2H), 7.10 (d,1H), 7.48 (d,1H), 8.42 (d,1H) |
| 47 | 2.36 (s,6H), 2.65 (s,3H), 3.97 (s,3H), 4.50 (s,2H), 7.17 (d,1H), 7.84 (s,1H), 8.24 (s,1H), 8.41 (d,1H) |
| 48 | 2.31 (s,3H), 2.34 (s,3H), 2.64 (s,3H), 4.71 (s,2H), 7.12 (d,1H), 7.59 (d,1H), 7.91 (k,1H), 8.22 (d,1H), 8.36 (d,1H) |
| 49 | 1.41 (t,3H), 2.27 (s,3H), 2.31 (s,3H), 3.87 (s,3H), 3.94 (k,2H), 4.41 (s,2H), 6.89 (k,1H), 7.12 (d,1H), 7.50 (d,1H), 8.35 (s,1H) |
| 50 | 1.17 (t,3H), 2.61 (k,2H), 2.69 (s,3H), 3.93 (s,6H), 4.43 (s,2H), 7.00 (s,1H), 7.45 (s,1H), 8.26 (s,1H), 8.35 (s,1H) |

The starting materials in the Examples 1–50 were prepared in accordance with the following:

(1) a substituted o-phenylenediamine was reacted with potassium etylxanthate (according to Org. Synth. Vol. 30, p. 56) to form a corresponding substituted 2-mercaptobenzimidazole;

(2) a substituted 2-chloromethylpyridine was prepared by reacting the corresponding 2-hydroxymethylpridine with thionylchloride;

(3) a substituted 2-chloromethylbenzimidazole was prepared by condensing the o-phenylenediamine with chloroacetic acid.

The following examples illustrate how the compounds of the formula I can be incorporated in pharmaceutical compositions:

EXAMPLE 51

Syrup

A syrup containing 2% (weight per volume) of active substance was prepared from the following ingredients:

| | |
|---|---|
| 2-[2-(3,5-dimethyl-4-methoxy)pyridylmethylthio]-(5-acetyl-6-methyl)benzimidazole.HCl | 2.0 g |
| Saccharin | 0.6 g |
| Sugar | 30.0 g |
| Glycerin | 5.0 g |
| Flavouring agent | 0.1 g |
| Ethanol 96% | 10.0 ml |
| Distilled water (sufficient to obtain a final volume of 100 ml) | |

Sugar, saccharin and the acid addition salt were dissolved in 60 g of warm water. After cooling, glycerin and a solution of flavouring agents dissolved in ethanol were added. To the mixture water was added to obtain a final volume of 100 ml.

The above given active substance may be replaced with other pharmaceutically acceptable acid addition salts.

EXAMPLE 52

Tablets

2-[2-(3,5-dimethyl-4-methoxy)pyridylmethylthio]-(5-methoxy)benzimidazole.HCl (250 g) was mixed with lactose (175.8 g), potato starch (169.7 g) and colloidal silicic acid (32 g). The mixture was moistened with 10% solution of gelatin and was ground through a 12-mesh sieve. After drying, potato starch (160 g), talc (50 g) and magnesium stearate (5 g) were added and the mixture thus obtained was pressed into tablets (10.000), with each tablet containing 25 mg of active substance. Tablets can be prepared that contain any desired amount of the active ingredient.

EXAMPLE 53

Tablets

Granules were prepared from 2-[2-(3,5-dimethyl-4-methoxy)pyridylmethylthio]-(5-carbomethoxy-6-methyl)benzimidazole base (250 g), lactose (175.9 g) and an alcoholic solution of polyvinylpyrrolidone (25 g). After drying, the granules were mixed with talc (25 g), potato starch (40 g), and magnesium stearate (2.50 g) and were pressed into 10.000 tablets. These tables are first coated with a 10% alcoholic solution of shellac and thereupon with an aqueous solution containing saccharose (45%), gum arabic (5%), gelatin (4%), and dyestuff (0.2%). Talc and powdered sugar were used for powdering after the first five coatings. The coating was then covered with a 66% sugar syrup and polished with a solution of 10% carnauba wax in carbon tetrachloride.

EXAMPLE 54

Solution for injection

2-[2-(3,5-dimethyl-4-methoxy)pyridylmethylthio]-(5-acetyl-6-methyl)benzimidazole hydrochloride (1 g), sodium chloride (0.6 g) and ascorbic acid (0.1 g) were dissolved in sufficient amount of distilled water to give 100 ml of solution. This solution, which contains 10 mg of active substance for each ml, was used in filling ampoules, which were sterilized by heating at 120° C. for 20 minutes.

BIOLOGICAL TESTS

Gastric Acid Secretion Inhibiting Effect on Conscious Dogs

Test Method

Chronic gastric fistula dogs (Heidenhain pouch dogs) were used. These dogs have been surgically provided with a gastric cannula in the pouch. Following a 4 weeks' recovery period after surgery, tests were performed once a week on each dog. Food and water were withdrawn 18 hours before each test.

Gastric acid secretion was induced by continuous infusion of histamine at individual doses (100–300 μmol/kg, h), resulting in submaximal secretion of gastric acid. At least 2 hours after onset of stimulation, when the gastric acid secertion had reached a steady level, the test compounds in the form of free base suspended in 0.5% Methocel ® (90 HG, 15.000, Dow Chem. corp.), were given orally by stomach tube. The gastric juice was collected by free flow from the gastric cannula in consecutive 30 minutes samples for 3 hours. The samples were titrated to pH 7.0 with 0.1M NaOH using a Radio-meter automatic titrator and the acid output was calculated.

The percent inhibition of acid secretion was calculated by comparing in each dog the acid output in the tests to the acid output in control tests when only the vehicle was given.

The test results are given in Table 6 below.

TABLE 6

Gastric acid secretion inhibiting effect on conscious dogs

Test compound

| $R^1$ | $R^2$ | R | $R^3$ | $R^4$ | $R^5$ | Dose (μmol/kg) | Effect (% inhibition) |
|---|---|---|---|---|---|---|---|
| 5-OCH$_3$ | H | H | CH$_3$ | OCH$_3$ | CH$_3$ | 2 | 75 |
| 5-COOCH$_3$ | H | H | CH$_3$ | OCH$_3$ | CH$_3$ | 8 | 50 |
| 5-COOCH$_3$ | 6-CH$_3$ | H | CH$_3$ | OCH$_3$ | CH$_3$ | 2 | 80 |
| 5-COCH$_3$ | 6-CH$_3$ | H | CH$_3$ | OCH$_3$ | CH$_3$ | 2 | 35 |
| 5-COCH$_3$ | H | H | CH$_3$ | OCH$_3$ | CH$_3$ | 8 | 90 |
| 5-CH$_3$ | H | H | CH$_3$ | OCH$_3$ | CH$_3$ | 2 | 60 |
| 5-COCH$_3$ | 6-CH$_3$ | H | H | CH$_3$ | CH$_3$ | 8 | 80 |
| 5-OCH$_3$ | H | H | CH$_3$ | CH$_3$ | CH$_3$ | 2 | 75 |

Comment to the Test Results

It is seen in Table 6 that the tested compounds after oral administration exhibited a high inhibiting effect on the gastric secretion.

What we claim is:

1. A pharmaceutical preparation for treating gastrointestinal inflammatory disease in mammals containing as an active ingredient a compound of the formula

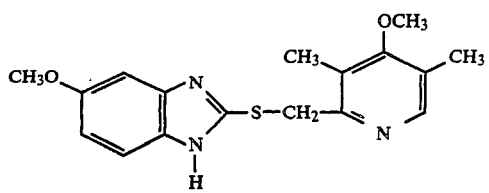

or a therapeutically acceptable salt thereof.

2. A method for inhibiting gastric acid secretion in mammals comprising administering to mammals in need of such treatment a pharmaceutical preparation containing as an active ingredient a compound of the formula

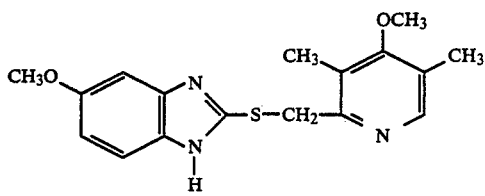

or a therapeutically acceptable salt thereof, together with a pharmaceutically acceptable carrier, said compound being present in an amount sufficient to inhibit gastric acid secretion in mammals.

3. A method for the treatment of gastrointestinal inflammatory diseases in mammals comprising administering to mammals suffering from the disease a pharmaceutical preparation containing as an active ingredient a compound of the formula

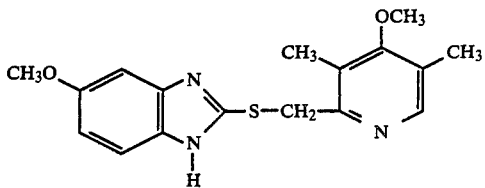

or a therapeutically acceptable salt thereof, together with a pharmaceutically acceptable carrier, said compound being present in an amount sufficient to inhibit gastric acid secretion in mammals.

* * * * *

UNITED STATES PATENT AND TRADEMARK OFFICE
CERTIFICATE OF CORRECTION

PATENT NO. : 4,746,667

DATED : 5/24/88

INVENTOR(S) : Enar I. Carlsson et al.

Page 1 of 2

It is certified that error appears in the above-identified patent and that said Letters Patent is hereby corrected as shown below:

<u>Col. 2, following line 14</u>
insert the following paragraph:
--In addition, the compounds of formula I are stable in their solid form, i.e., they have a long shelf life.--;

<u>Col 2, line 62</u>, "R" should appear on line 60, preceding $R^3$, $R^4$, and $R^5$";

<u>Col 3, line 5</u>, "R" should appear on line 3, preceding $R^3$, $R^4$, and $R^5$";

<u>Col. 3 line 28</u> "alkanyol" should be --alkanoyl--

<u>Col. 4, line 59</u> previosly should be --previously--

<u>Col. 7, line 21</u>, respektively" should be --respectively--

<u>Col. 7, line 48</u>, respektively" should be --respectively--

<u>Col. 8, line 31</u> "reduktion" should be --reduction--

<u>Col. 9, line 48</u>, "tatanium" should read --titanium--; and

UNITED STATES PATENT AND TRADEMARK OFFICE
CERTIFICATE OF CORRECTION

PATENT NO. : 4,746,667
DATED : May 24, 1988
INVENTOR(S) : Enar I. Carlsson et al It is certified that error appears in the above-identified patent and that said Letters Patent is hereby corrected as shown below:

Col. 15, line 5 "secertion" should read --secretion--.

Signed and Sealed this

Eighth Day of November, 1988

*Attest:*

DONALD J. QUIGG

*Attesting Officer*  *Commissioner of Patents and Trademarks*